(12) United States Patent
Murata et al.

(10) Patent No.: US 9,303,003 B2
(45) Date of Patent: Apr. 5, 2016

(54) PROCESS FOR PRODUCING GLYCIDYL (METH)ACRYLATE

(71) Applicant: MITSUBISHI RAYON CO., LTD., Chiyoda-ku (JP)

(72) Inventors: Naoshi Murata, Otake (JP); Hiroyuki Mori, Otake (JP)

(73) Assignee: MITSUBISHI RAYON CO., LTD., Chiyoda-ku (JP)

( * ) Notice: Subject to any disclaimer, the term of this patent is extended or adjusted under 35 U.S.C. 154(b) by 0 days.

(21) Appl. No.: 14/434,211

(22) PCT Filed: Mar. 11, 2014

(86) PCT No.: PCT/JP2014/056245
§ 371 (c)(1),
(2) Date: Apr. 8, 2015

(87) PCT Pub. No.: WO2014/148301
PCT Pub. Date: Sep. 25, 2014

(65) Prior Publication Data
US 2015/0291544 A1    Oct. 15, 2015

(30) Foreign Application Priority Data

Mar. 22, 2013  (JP) ................................. 2013-060041
Oct. 30, 2013  (JP) ................................. 2013-225341

(51) Int. Cl.
*C07D 301/27*   (2006.01)
*C07D 301/30*   (2006.01)
*C07D 303/16*   (2006.01)

(52) U.S. Cl.
CPC ............ *C07D 301/30* (2013.01); *C07D 303/16* (2013.01)

(58) Field of Classification Search
CPC ............................ C07D 301/30; C07D 303/16

USPC .......................................................... 549/515
See application file for complete search history.

(56) References Cited

U.S. PATENT DOCUMENTS

| | | | | |
|---|---|---|---|---|
| 2,537,981 A | * | 1/1951 | Edwards ....................... | 549/515 |
| 4,755,262 A | * | 7/1988 | Matsunaga et al. ................ | 203/6 |
| 5,183,539 A | * | 2/1993 | Honma et al. .................. | 203/38 |
| 5,380,884 A | | 1/1995 | Hosokawa et al. | |
| 5,481,012 A | | 1/1996 | Caubere et al. | |

FOREIGN PATENT DOCUMENTS

| | | |
|---|---|---|
| JP | 57 21380 | 2/1982 |
| JP | 5 92962 | 4/1993 |
| JP | 7 2818 | 1/1995 |
| JP | 7 118251 | 5/1995 |
| JP | 8 188575 | 7/1996 |
| JP | 9 59269 | 3/1997 |
| JP | 9 132571 | 5/1997 |
| JP | 9 301966 | 11/1997 |
| JP | 2010 126453 | 6/2010 |

OTHER PUBLICATIONS

Fort, et al., "Synthesis of Epoxy (Meth)acrylic Esters by Selective Epoxidation of Unsaturated (Meth)acrylic Esters using the System $H_2O_2$—$Na_2WO_4$ under Phase Transfer Catalysis", Tetrahedron, vol. 48, No. 24, (1992) pp. 5099-5110.
International Search Report Issued Apr. 15, 2014 in PCT/JP14/056245 Filed Mar. 11, 2014.

* cited by examiner

*Primary Examiner* — T. Victor Oh
(74) *Attorney, Agent, or Firm* — Oblon, McClelland, Maier & Neustadt, L.L.P.

(57) ABSTRACT

Provided is glycidyl(meth)acrylate which is reduced in the content of impurities including chlorine. This process comprises reacting epichlorohydrin with an alkali metal (meth)acrylate in the presence of a catalyst to produce glycidyl (meth)acrylate, the process including a step in which the reaction is conducted while making a Bronsted acid present in the reaction system in an amount of 0.0001-0.08 mol per mol of the alkali metal (meth)acrylate.

11 Claims, No Drawings

PROCESS FOR PRODUCING GLYCIDYL (METH)ACRYLATE

TECHNICAL FIELD

The present invention relates to a process for producing glycidyl(meth)acrylate.

BACKGROUND ART

As a representative example of a process for synthesizing glycidyl(meth)acrylate, a process of using epichlorohydrin as a raw material can be mentioned. Broadly classified, there are two processes as described below.

The first process is a process in which epichlorohydrin and an alkali metal salt of (meth)acrylic acid are reacted with each other in the presence of a catalyst to synthesize glycidyl (meth)acrylate (Patent Document 1). The second process is a process in which epichlorohydrin and (meth)acrylic acid are reacted with each other in the presence of a catalyst followed by cyclization using an aqueous alkali solution to synthesize glycidyl(meth)acrylate (Patent Document 2).

The process described in Patent Document 1 exhibits higher yield than the process described in Patent Document 2.

CITATION LIST

Patent Document

Patent Document 1: JP 7-2818 A
Patent Document 2: JP 7-118251 A

DISCLOSURE OF THE INVENTION

Problem to be Solved by the Invention

However, since epichlorohydrin as a raw material has an epoxy group with high reactivity, many side reactions can occur. In particular, impurities containing chlorine, which are not easily separated by distillation, are generated as a side product, and thus inhibiting the generation of such impurities remains as a problem to be solved. For such reasons, in a process for producing glycidyl(meth)acrylate, it has been required to reduce various known side products according to a simple and low-cost process.

An object of the present invention is to provide glycidyl (meth)acrylate which is reduced in the content of impurities containing chlorine.

Means for Solving Problem

The present invention is an invention which is related to the following [1] to [5].

[1] A process for producing glycidyl(meth)acrylate by reacting epichlorohydrin with an alkali metal salt of (meth) acrylic acid in the presence of a catalyst, the process including a step of performing the reaction while having Broensted acid present in a reaction system in an amount of 0.0001 mol to 0.08 mol per mol of the alkali metal salt of (meth)acrylic acid.

[2] The process for producing glycidyl(meth)acrylate described in [1], in which the Broensted acid is at least one of carboxylic acid and sulfonic acid.

[3] The process for producing glycidyl(meth)acrylate described in [2], in which the Broensted acid is at least one type selected from a group consisting of (meth)acrylic acid, benzoic acid, acetic acid, and methane sulfonic acid.

[4] The process for producing glycidyl(meth)acrylate described in any one of [1] to [3], the process further including a step of washing a reaction solution obtained by the reaction and maintaining a solution after the washing to separate an organic washed layer and a step of distilling a solution of the organic washed layer.

[5] Glycidyl(meth)acrylate containing impurities at 500 ppm or less in terms of a total amount of chlorine.

Effect of the Invention

According to the present invention, it is possible to provide glycidyl(meth)acrylate which is reduced in the content of impurities containing chlorine.

MODE(S) FOR CARRYING OUT THE INVENTION

The process according to the present invention is a process for producing glycidyl(meth)acrylate by reacting epichlorohydrin with an alkali metal salt of (meth)acrylic acid in the presence of a catalyst, and the process includes a step of performing the reaction while having Broensted acid present in the reaction system in an amount of 0.0001 mol to 0.08 mol per mol of the alkali metal salt of (meth)acrylic acid. According to the present invention, as the Broensted acid is present in an amount within the aforementioned range for the reaction between epichlorohydrin and an alkali metal salt of (meth) acrylic acid, generation of impurities containing chlorine like chloropropenyl(meth)acrylate is inhibited. Accordingly, glycidyl(meth)acrylate having reduced content of impurities containing chlorine, which are difficult to be separated by distillation, can be obtained. Further, the process of the present invention may include, in addition to the reaction step in which the aforementioned reaction is performed, a step of washing a reaction solution obtained by the reaction and maintaining a solution after the washing to separate an organic washed layer and a step of distilling a solution of the organic washed layer. Hereinbelow, each step of the process of the present invention is described in detail.

[Reaction Step]

The process according to the present invention includes a step of reacting epichlorohydrin with an alkali metal salt of (meth)acrylic acid in the presence of a catalyst. In the present invention, glycidyl(meth)acrylate is produced by a reaction between epichlorohydrin and an alkali metal salt of (meth) acrylic acid. According to the reaction of the present invention, a Broensted acid is present in the reaction system in an amount of 0.0001 mol to 0.08 mol per mol of the alkali metal salt of (meth)acrylic acid. As for the Broensted acid, at least one of carboxylic acid and sulfonic acid is preferable from the viewpoint of solubility in the reaction solution and easy handlability. Further, from the obtainability and cost, the Broensted acid is more preferably at least one selected from a group consisting of (meth)acrylic acid, benzoic acid, acetic acid, and methane sulfonic acid. Here, (meth)acrylic acid represents methacrylic acid or acrylic acid and the alkali metal salt of (meth)acrylic acid represents an alkali metal salt of methacrylic acid or an alkali metal salt of acrylic acid.

Examples of the alkali metal salt of (meth)acrylic acid which may be used include, although not particularly limited, sodium(meth)acrylic acid, potassium(meth)acrylic acid, lithium(meth)acrylic acid, and the like. It may be used either singly or in combination of two or more types.

The alkali metal salt of (meth)acrylic acid can be produced by neutralization of (meth)acrylic acid with an alkali metal hydroxide. Preferred examples of the alkali metal hydroxide include, although not particularly limited, sodium hydroxide, potassium hydroxide, lithium hydroxide, and the like. It may be used either singly or in combination of two or more types.

The mixing ratio between (meth)acrylic acid and an alkali metal hydroxide is as follows: the alkali metal hydroxide is preferably 0.9 to 1.1 mols, more preferably 0.95 to 1.05 mols, and even more preferably 0.99 to 1.01 mols per mol of (meth) acrylic acid. As the reaction solution to be obtained gets closer to neutral, the side reaction during the synthesis of glycidyl(meth)acrylate is inhibited more. At that time, if (meth)acrylic acid is mixed in a slightly excess amount than the alkali metal hydroxide, the (meth)acrylic acid as Broensted acid for the reaction with epichlorohydrin can be present in the amount range of the present invention, and therefore preferable. Furthermore, when alkali metal hydroxide is mixed in a slightly excess amount compared to the (meth) acrylic acid, malodor of (meth)acrylic acid can be inhibited, and thus industrially preferable. However, there is also a case in which the excess alkali component causes a side reaction during the reaction with epichlorohydrin. For solving this problem, the process of the present invention in which Broensted acid is allowed to be present is also effective. Meanwhile, when the produced alkali metal salt of (meth)acrylic acid contains alkali metal hydroxide, the Broensted acid is added such that Broensted acid is present in an amount of 0.0001 mol to 0.08 mol per mol of the alkali metal salt of (meth) acrylic acid, considering the neutralization of Broensted acid by alkali metal hydroxide. Since the amount of the alkali metal hydroxide used for neutralization can be calculated based on an injection amount of each raw material, the amount of Broensted acid required for neutralization of the alkali metal hydroxide can be also calculated.

For neutralization of (meth)acrylic acid with alkali metal hydroxide, it is possible to use a solvent. From the viewpoint of solubility, it is preferable to use alcohol like methanol or water as a solvent. When a solvent is used, the solvent can be removed after the neutralization. As for a process for removing the solvent, a known process can be used, and for example, distillation, a spray dryer or the like can be used.

The temperature of the reaction solution at the time of neutralization is preferably –10° C. to 80° C. from the viewpoint of polymerization inhibition and cooling efficiency. It is also possible to add a polymerization inhibitor for inhibiting polymerization.

According to the present invention, Broensted acid is present in an amount of 0.0001 mol to 0.08 mol per mol of the alkali metal salt of (meth)acrylic acid when epichlorohydrin and an alkali metal salt of (meth)acrylic acid are reacted with each other in the presence of a catalyst. As the Broensted acid is present in an amount of 0.0001 mol or more, the side reaction is sufficiently inhibited. Further, as the Broensted acid is present in an amount of 0.08 mol or less, low cost can be achieved and also the side reaction is sufficiently inhibited. For the aforementioned step, it is preferable that Broensted acid be present in an amount of 0.001 mol to 0.075 mol per mol of an alkali metal salt of (meth)acrylic acid, more preferably 0.005 mol to 0.07 mol, and even more preferably 0.01 mol to 0.05 mol. Meanwhile, the amount of Broensted acid present in the reaction system relative to the alkali metal salt of (meth)acrylic acid can be calculated from an injection amount of each raw material.

In particular, as the Broensted acid is present within the aforementioned range, generation of impurities containing chlorine is inhibited. Examples of the impurities containing chlorine include chloropropenyl(meth)acrylate, which is represented by the following formula (1), and 1,3-dichloro-2-propanol.

[Chem. 1]

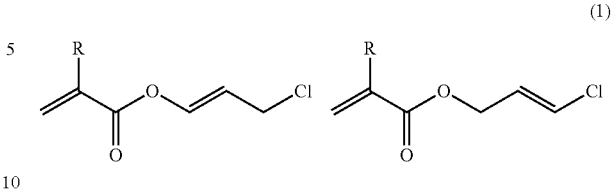

(1)

In the above formula (1), R represents hydrogen or a methyl group. Since chloropropenyl(meth)acrylate represented by the above formula (1) particularly has a small difference in boiling point compared to glycidyl(meth)acrylate, it cannot be separated by distillation. As a result, it is incorporated in a product. In this regard, the inventors of the present invention found that, by having Broensted present acid according to addition of Broensted acid at the time of injecting raw materials, the amount of a side product like chloropropenyl(meth)acrylate, which is represented by the above formula (1), can be reduced. It is believed that, since an increase of chloropropenyl(meth)acrylate has been confirmed in the presence of a trace amount of an alkaline compound, the Broensted acid has an effect of neutralizing an alkaline compound which is present in a trace amount.

With regard to the Broensted acid to be present in the reaction system, the presence can be achieved by using an excess amount of (meth)acrylic acid during preparation of an alkali metal salt of (meth)acrylic acid, or by adding Broensted acid to the reaction system either before the start of the reaction or during the first half of the reaction. As described herein, the first half of the reaction indicates a period from mixing raw materials followed by heating and achieving a predetermined temperature to have the conversion ratio of 50% by mol or less based on alkali metal salt of (meth)acrylic acid.

The reaction between epichlorohydrin and an alkali metal salt of (meth)acrylic acid is performed in the presence of a catalyst. Examples of the catalyst which may be used include a quaternary ammonium salt and an ion exchange resin having the salt. Examples of the quaternary ammonium salt which may be used include tetraalkyl ammonium salt including tetramethyl ammonium chloride, tetramethyl ammonium bromide, tetraethyl ammonium chloride, tetraethyl ammonium bromide, tetrabutyl ammonium chloride, and tetrabutyl ammonium bromide. As for the ion exchange resin, a commercially available strong-basic anion exchange resin can be used. It may be used either singly or in combination of two or more types.

For the reaction between epichlorohydrin and an alkali metal salt of (meth)acrylic acid and neutralization reaction between (meth)acrylic acid and alkali metal hydroxide, a polymerization inhibitor can be used for inhibiting polymerization. Examples of the polymerization inhibitor which may be used include a phenol type such as hydroquinone or paramethoxy phenol, an amine type such as phenothiazine, and N-oxyl type such as 4-hydroxy-2,2,6,6-tetramethylpiperidine-N-oxyl (HO-TEMPO). It may be used either singly or in combination of two or more types. Furthermore, it is also preferable to bubble oxygen or air during the reaction for preventing the polymerization.

The reaction temperature for the reaction between epichlorohydrin and an alkali metal salt of (meth)acrylic acid can be suitably selected depending on an amount of the catalyst to be used. Preferably, it is 40° C. to 150° C. More preferably, it is 50° C. to 140° C. As the reaction temperature is 40° C. or higher, sufficient reaction rate is obtained. Further, as the reaction temperature is 150° C. or lower, generation of a side product can be inhibited.

The molar ratio between epichlorohydrin and an alkali metal salt of (meth)acrylic acid that are used for the reaction between epichlorohydrin and an alkali metal salt of (meth) acrylic acid is not particularly limited. However, it is preferable that epichlorohydrin be 1.0 mol to 20.0 mols per mol of the alkali metal salt of (meth)acrylic acid. More preferably, it is 1.5 mols to 10.0 mols. As the epichlorohydrin is present at 1.0 mol or more, the conversion rate based on alkali metal salt of (meth)acrylic acid can be improved. Further, as the epichlorohydrin is present at 20.0 mols or less, the yield amount per reaction batch can be increased.

The amount of the catalyst used for the reaction between epichlorohydrin and an alkali metal salt of (meth)acrylic acid is preferably 0.01 mol to 10 mols per mol of the alkali metal salt of (meth)acrylic acid. More preferably, it is 0.05 mol to 5 mols. As the amount of the catalyst is 0.01 mol or more per mol of the alkali metal salt of (meth)acrylic acid, sufficient reaction rate is obtained. Further, as the amount of the catalyst is 10 mols or less per mol of the alkali metal salt of (meth) acrylic acid, generation of a side product can be inhibited.

The amount of the polymerization inhibitor used for the reaction between epichlorohydrin and an alkali metal salt of (meth)acrylic acid is preferably 10 ppm by mass to 10000 ppm by mass relative to the mass of the alkali metal salt of (meth)acrylic acid. More preferably, it is 50 ppm by mass to 5000 ppm by mass. As the amount of the polymerization inhibitor is 10 ppm by mass or more, the polymerization can be sufficiently inhibited. Further, as the amount of the polymerization inhibitor is 10000 ppm by mass or less, an occurrence of quality deterioration caused by coloration of a product or the like can be inhibited.

[Washing Step]

The process according to the present invention preferably includes a step of washing a reaction solution which is obtained by the reaction between epichlorohydrin and an alkali metal salt of (meth)acrylic acid and maintaining the solution after the washing to separate an organic washed layer. In the reaction solution after completion of the reaction, alkali metal chlorides, catalyst, excess epichlorohydrin, side products, or the like are present in addition to glycidyl(meth) acrylate. By washing the reaction solution with washing water, it is possible to dissolve alkali metal chlorides, catalyst, specific side products in an aqueous layer for separation and removal of them.

As the washing water used for washing, water or an aqueous solution containing alkaline compound dissolved therein can be used. Examples of the alkaline compound include, although not particularly limited, alkali metal hydroxide, alkali metal carbonate, and alkali metal hydrogen carbonate. Specific examples thereof include sodium hydroxide, potassium hydroxide, sodium carbonate, potassium carbonate, sodium hydrogen carbonate, and potassium hydrogen carbonate. It may be used either singly or in combination of two or more types. The amount of the alkaline compound contained in the washing water is preferably 0 part by mass to 50 parts by mass per 100 parts by mass of water constituting the washing water. More preferably, it is 0.1 part by mass to 30 parts by mass. Even more preferably, it is 0.2 part by mass to 20 parts by mass. As the amount of the alkaline compound is within the aforementioned range, generation of a side product can be fully inhibited.

The amount of the washing water used for the washing step is preferably an amount which allows sufficient dissolution of the alkali metal chloride, catalyst, or the like. Specifically, the amount of the washing water is preferably 160 g to 2000 g per mol of the alkali metal salt of (meth)acrylic acid. More preferably, it is 180 g to 1500 g. As the amount of the washing water is 160 g or more, the alkali metal chloride, catalyst, or the like can be sufficiently dissolved. Furthermore, as the amount of the washing water is 2000 g or less, the productivity is enhanced.

At the time of the washing, stirring can be performed according to a known process for stirring. For example, it is possible that the reaction solution and the washing water are sufficiently stirred and admixed with each other by using a stirrer having a stirring blade. The time for stirring is not particularly limited. For example, it can be 3 minutes or longer but 60 minutes or shorter.

By maintaining the reaction solution and washing water after mixing by stirring, they can be separated into a washed organic layer and an aqueous layer. The solution of the washed organic layer can be purified during the following distillation step.

[Distillation Step]

The process according to the present invention may include a step of distilling a solution of the organic washed layer. By distilling the solution of the washed organic layer, glycidyl (meth)acrylate can be obtained with high purity. Distillation of the solution of the organic washed layer can be performed according to a known process. From the viewpoint of obtaining glycidyl(meth)acrylate with even higher purity, it is preferable to perform rectification using a tower. The distillation can be either a batch mode or a continuous mode. Fine distillation according to a batch mode is described hereinbelow.

Since glycidyl(meth)acrylate is a polymerizable monomer, the polymerization can be inhibited by performing distillation at lower temperature under reduced pressure. From this point of view, the temperature of a distillation vessel is preferably 160° C. or less, and more preferably 150° C. or less. Meanwhile, from the viewpoint of distillation efficiency, the temperature of a distillation vessel is preferably 60° C. or more, and more preferably 70° C. or more. Further, from the viewpoint of decompression limit, the degree of decompression is preferably 0.1 kPa or more, and more preferably 0.5 kPa or more. Meanwhile, from the viewpoint of lowering the temperature, the degree of decompression is preferably 50 kPa or less, and more preferably 30 kPa or less.

For inhibiting the polymerization, a known polymerization inhibitor can be supplied to inside of a distillation vessel and inside of a tower. Examples of the polymerization inhibitor which may be used include a phenol type such as hydroquinone or paramethoxy phenol and N-oxyl type such as 4-hydroxy-2,2,6,6-tetramethylpiperidine-N-oxyl (HO-TEMPO). It may be used either singly or in combination of two or more types. Furthermore, it is also preferable to bubble oxygen or air during the distillation for preventing the polymerization.

For a rectifying operation using a tower, a known process can be used. As for the tower, a known apparatus like a tray type and a packed tower using a packing material can be used. By controlling the refluxing ratio during a distilling operation, the purity can be improved. Specifically, from the viewpoint of obtaining the purity and productivity, the reflux ratio is preferably in the range of 0.1 to 10. More preferably, it is in the range of 0.3 to 3.

According to the process of the present invention, glycidyl (meth)acrylate containing impurities at 500 ppm or less in terms of the total amount of chlorine can be obtained. Namely, according to the process of the present invention, it is possible to obtain glycidyl(meth)acrylate in which compounds (impurities) containing chlorine (Cl) is contained at 500 ppm or less in terms of the total amount of chlorine (Cl). Herein, the impurities include impurities containing chlorine and impurities not containing chlorine. However, some of the impurities containing chlorine are not easily removed even by distillation, and they eventually remain as impurities. As such, in the present invention, content of the impurities is described as the total amount of chlorine contained in glycidyl(meth)acrylate. Meanwhile, in distillation eluent obtained after the distillation, there is almost no chlorine other than the chlorine contained in the impurities. The glycidyl(meth)acrylate may contain the impurities at 450 ppm or less in terms of the total amount of chlorine. The impurities may be contained at 400 ppm or less in terms of the total amount of chlorine. The impurities may be contained at 300 ppm or less in terms of the total amount of chlorine. Meanwhile, the amount of the impurities as the total amount of chlorine contained in glycidyl(meth)acrylate is preferably as small as possible. It can be also 0 ppm. Further, the total amount of chlorine is a value that is obtained by heating distillation eluent to 100 to 900° C. by using a sample combustion device QF-02 (trade name, manufactured by Mitsubishi Chemical Corporation) for combustion, allowing gas to get absorbed in an absorbing pipe, and performing IC (ion chromatography) analysis for quantification.

EXAMPLES

Hereinbelow, the present invention is described in detail in view of the examples. However, the present invention is not limited to them. For the analysis of each compound in the examples and comparative examples, gas chromatography (GC) was used.

[Process for Measuring Total Amount of Chlorine]

By using sample combustion device QF-02 (trade name, manufactured by Mitsubishi Chemical Corporation), eluent obtained after distillation was heated to 100 to 900° C. for combustion. Then, after allowing gas to get absorbed in an absorbing pipe, IC (ion chromatography) analysis was performed to measure the total amount of chlorine.

Example 1

In 387.4 g (4.5 mol) of methacrylic acid, 0.04 g of benzoyl ester of HO-TEMPO was dissolved as a polymerization inhibitor. The resulting solution and an aqueous solution in which 180 g (4.5 mol) of sodium hydroxide is dissolved in 420 g of water were admixed with each other. The mixture solution was spray-dried using hot air. Accordingly, sodium methacrylate was obtained. Meanwhile, no methacrylic acid was detected from this sodium methacrylate.

A 50 ml flask equipped with a thermometer, an air inlet, a stirring blade, and a condenser was prepared. To the flask, 4.435 g (0.041 mol) of sodium methacrylate obtained above, 0.0185 g (0.00017 mol) of tetramethyl ammonium chloride as a catalyst, 0.0005 g of benzoyl ester of HO-TEMPO as a polymerization inhibitor, 19.8 g (0.214 mol) of epichlorohydrin, and 0.073 g (0.000842 mol) of methacrylic acid were added. The reaction solution was heated to 90° C. in an oil bath while air was introduced to the flask at rate of 10 ml/minute and the reaction solution was stirred. After the temperature of the reaction solution reaches 90° C., the heating was continued additionally for 3 hours such that the temperature of the reaction solution reaches 89 to 91° C. After that, the reaction solution was cooled to room temperature and filtered. The filtrate was subjected to GC analysis. As a result, it was found that the area percentage of chloropropenyl methacrylate (CPMA) is 0.046%, the area percentage of glycidol is 0.756%, and the area percentage of 1,3-dichloro-2-propanol (DCP) is 0.035%. Further, the area percentage of impurities with high boiling point (diesters, triesters, and chlorohydrin propyl methacrylate in total) was 4.523% and the area percentage of glycidyl methacrylate (GMA) was 93.6%.

After that, the obtained reaction solution was washed. Specifically, 8.8 g of 0.57% by mass aqueous solution of sodium hydroxide was first added to the reaction solution. The resulting mixture solution was stirred in a glass vessel equipped with a stirring blade for 15 minutes at stirring speed of 250 rpm to wash the reaction solution. After that, it was transferred to a separatory funnel and allowed to stand for 30 minutes for layer separation. Further, the solution of the washed organic layer which has been obtained by washing was distilled. Specifically, 21 g of the solution of the washed organic layer was added to a flask and subjected to short path distillation. Excess epichlorohydrin was eluted and collected. Then, the main part was eluted at the internal temperature of 94 to 124° C., the tower top temperature of 71 to 85° C., and the pressure of 1.33 to 2.95 kPa. Accordingly, 4 g of the distillation eluent was obtained. The obtained distillation eluent was subjected to GC analysis. The area percentage of CPMA was 0.046%, the area percentage of glycidol was 0.076%, and the area percentage of DCP was 0.002%. Further, the area percentage of impurities with high boiling point was 0.000% and the area percentage of GMA was 99.8%. Further, based on the measurement of total amount of chlorine as described above, it was confirmed that impurities are contained at 214 ppm in the distillation eluent in terms of the total amount of chlorine.

Examples 2 to 13 and Comparative Examples 1 to 5

After performing the reaction, washing, and distillation, GC analysis and measurement of total amount of chlorine were carried out in the same manner as Example 1 except that the type and amount of Broensted acid, which is added at the time of injecting raw materials in the reaction step, are modified to those described in Table 1. The results are described in Table 1.

TABLE 1

| | | Broensted acid | Content of | Reaction solution | | | | |
|---|---|---|---|---|---|---|---|---|
| | Type of Broensted acid | (mol)/Sodium methacrylate (mol) | Broensted acid (relative to sodium methacrylate) (%) | CPMA (GC area %) | Glycidol (GC area %) | DCP (GC area %) | Components with high boiling point (GC area %) | GMA (GC area %) |
| Example 1 | Methacrylic acid | 0.0205 | 2.1 | 0.046 | 0.756 | 0.035 | 4.523 | 93.6 |
| Example 2 | Methacrylic acid | 0.0102 | 1.0 | 0.051 | 1.477 | 0.011 | 5.158 | 92.1 |
| Example 3 | Methacrylic acid | 0.0309 | 3.1 | 0.061 | 0.441 | 0.056 | 4.301 | 95.1 |
| Example 4 | Methacrylic acid | 0.0411 | 4.1 | 0.021 | 0.196 | 0.120 | 4.148 | 95.3 |
| Example 5 | Methacrylic acid | 0.0500 | 5.0 | 0.021 | 0.200 | 0.256 | 4.085 | 94.5 |
| Example 6 | Methacrylic acid | 0.0010 | 0.1 | 0.079 | 1.046 | 0.012 | 4.283 | 93.6 |

TABLE 1-continued

| | | | | | | | |
|---|---|---|---|---|---|---|---|
| Example 7 | Benzoic acid | 0.0050 | 0.5 | 0.076 | 0.805 | 0.014 | 2.953 | 94.3 |
| Example 8 | Benzoic acid | 0.0098 | 1.0 | 0.059 | 0.996 | 0.044 | 4.017 | 94.1 |
| Example 9 | Benzoic acid | 0.0488 | 4.9 | 0.022 | 0.989 | 0.127 | 5.755 | 93.6 |
| Example 10 | Acetic acid | 0.0050 | 0.5 | 0.085 | 1.167 | 0.036 | 3.491 | 93.6 |
| Example 11 | Acetic acid | 0.0098 | 1.0 | 0.070 | 1.155 | 0.060 | 4.579 | 93.0 |
| Example 12 | Acetic acid | 0.0488 | 4.9 | 0.024 | 1.615 | 0.208 | 4.598 | 93.5 |
| Example 13 | Methane sulfonic acid | 0.0098 | 1.0 | 0.027 | 0.149 | 0.045 | 2.288 | 96.7 |
| Comparative Example 1 | — | 0 | 0 | 0.196 | 0.992 | 0.030 | 3.897 | 93.7 |
| Comparative Example 2 | Methacrylic acid | 0.0822 | 8.2 | 0.019 | 0.214 | 0.824 | 5.953 | 92.6 |
| Comparative Example 3 | Acetic acid | 0.1000 | 10.0 | 0.020 | 0.445 | 1.457 | 4.880 | 86.7 |
| Comparative Example 4 | Methane sulfonic acid | 0.1000 | 10.0 | 0.023 | 0.422 | 1.788 | 3.027 | 82.7 |
| Comparative Example 5 | Benzoic acid | 0.1000 | 10.0 | 0.020 | 0.408 | 0.999 | 8.045 | 76.085 |

| | Distillation eluent | | | | | |
|---|---|---|---|---|---|---|
| | CPMA (GC area %) | Glycidol (GC area %) | DCP (GC area %) | Components with high boiling point (GC area %) | GMA (GC area %) | Total amount of chlorine (ppm) |
| Example 1 | 0.046 | 0.076 | 0.002 | 0.000 | 99.8 | 214 |
| Example 2 | 0.051 | 0.148 | 0.002 | 0.000 | 99.6 | 218 |
| Example 3 | 0.061 | 0.044 | 0.009 | 0.000 | 99.9 | 345 |
| Example 4 | 0.021 | 0.020 | 0.018 | 0.000 | 99.9 | 275 |
| Example 5 | 0.021 | 0.020 | 0.039 | 0.000 | 99.9 | 486 |
| Example 6 | 0.079 | 0.105 | 0.002 | 0.000 | 99.4 | 336 |
| Example 7 | 0.076 | 0.081 | 0.002 | 0.000 | 99 8 | 304 |
| Example 8 | 0.059 | 0.100 | 0.007 | 0.000 | 99.9 | 284 |
| Example 9 | 0.022 | 0.100 | 0.020 | 0.000 | 99.9 | 264 |
| Example 10 | 0.085 | 0.117 | 0.006 | 0.000 | 99.9 | 376 |
| Example 11 | 0.070 | 0.116 | 0.009 | 0.000 | 99.9 | 353 |
| Example 12 | 0.024 | 0.162 | 0.032 | 0.000 | 99.9 | 405 |
| Example 13 | 0.027 | 0.015 | 0.007 | 0.000 | 99.9 | 157 |
| Comparative Example 1 | 0.196 | 0.099 | 0.002 | 0.000 | 99.4 | 823 |
| Comparative Example 2 | 0.019 | 0.021 | 0.127 | 0.000 | 99.8 | 1387 |
| Comparative Example 3 | 0.020 | 0.045 | 0.224 | 0.000 | 99.8 | 2358 |
| Comparative Example 4 | 0.023 | 0.042 | 0.275 | 0.000 | 99.8 | 2893 |
| Comparative Example 5 | 0.020 | 0.041 | 0.154 | 0.000 | 99.9 | 1387 |

This application claims priority to Japanese Patent Application No. 2013-60041 which has been filed on Mar. 22, 2013 and Japanese Patent Application No. 2013-225341 which has been filed on Oct. 30, 2013, and the entire contents of their disclosure are incorporated herein by reference.

Hereinabove, the present invention is described in view of the embodiments and examples. However, it is evident that the present invention is not limited to those embodiments and examples, and various modifications that can be understood by a person skilled in the art can be made within the constitution, or specifically, within the scope of the present invention.

INDUSTRIAL APPLICABILITY

Glycidyl(meth)acrylate produced by the process of the present invention can be used for various kinds of paint, adhesives, adhesive material, various reactive monomers, or the like.

The invention claimed is:

1. A process, comprising:
    reacting epichlorohydrin with an alkali metal salt of (meth)acrylic acid in the presence of a catalyst, thereby producing glycidyl (meth)acrylate,
    wherein reacting the epichlorohydrin with the alkali metal salt of (meth)acrylic acid is in the presence of a Broensted acid in a reaction system in an amount of 0.0001 mol to 0.08 mol per mol of the alkali metal salt of (meth)acrylic acid,
    wherein a total content of chloropropenyl (meth)acrylate and 1,3-dichloro-2-propanol in a reaction solution is 2770 ppm or less,
    wherein the catalyst is a quaternary ammonium salt and/or an ion exchange resin comprising a quaternary ammonium salt.

2. The process of claim 1, wherein a content of chloropropenyl (meth)acrylate in the reaction solution is 850 ppm or less.

3. The process of claim 1, wherein a content of 1,3-dichloro-2-propanol in the reaction solution is 2560 ppm or less.

4. The process of claim 2, wherein a content of 1,3-dichloro-2-propanol in the reaction solution is 2560 ppm or less.

5. The process of claim 1, wherein the catalyst is a quaternary ammonium salt.

6. The process of claim 1, wherein the catalyst is an ion exchange resin comprising a quaternary ammonium salt.

7. The process of claim 1, wherein the Broensted acid is (meth)acrylic acid, benzoic acid, acetic acid, methane sulfonic acid, or any combination thereof.

8. The process of claim 1, wherein a total chlorine content is 486 ppm or less.

9. The process of claim 1, further comprising neutralizing (meth)acrylic acid with an alkali metal hydroxide, thereby obtaining the alkali metal salt of (meth)acrylic acid, prior to the reacting of epichlorohydrin with the alkali metal salt of (meth)acrylic acid,
   wherein a molar mixing ratio of the (meth)acrylic acid to the alkali metal hydroxide is from 0.9 to 1.1.

10. The process of claim 1, wherein the process does not comprise distillation.

11. The process of claim 1, wherein the process further comprises washing then distilling the glycidyl (meth)acrylate.

\* \* \* \* \*